United States Patent [19]

Neward

[11] 4,064,909

[45] Dec. 27, 1977

[54] SLIDE VALVE APPARATUS

[76] Inventor: Theodore C. Neward, c/o Neward Enterprises, 976 W. 9th St., Upland, Calif. 91786

[21] Appl. No.: 626,119

[22] Filed: Oct. 28, 1975

Related U.S. Application Data

[63] Continuation-in-part of Ser. No. 377,801, July 9, 1973, abandoned.

[51] Int. Cl.$^2$ .............................................. F16K 3/316
[52] U.S. Cl. ............................... 137/625.48; 251/367; 251/125; 251/319; 251/321
[58] Field of Search ........................ 222/561; 251/125; 137/625.48; 251/367, 319, 321

[56] References Cited

U.S. PATENT DOCUMENTS

| | | | |
|---|---|---|---|
| 1,640,481 | 8/1927 | Collins | 222/561 X |
| 1,754,482 | 4/1930 | Nicholls | 222/561 X |
| 1,769,814 | 7/1930 | Wilson | 222/561 |
| 2,024,037 | 12/1935 | Geis | 222/561 X |
| 2,071,960 | 2/1937 | Wilson | 222/561 X |
| 2,839,228 | 6/1958 | Levine | 222/561 X |
| 2,916,189 | 12/1959 | Christenson | 222/561 X |
| 3,132,669 | 5/1964 | Feldsted | 137/625.48 |
| 3,323,774 | 6/1967 | Wilson | 251/125 |
| 3,773,082 | 11/1973 | Davis | 137/625.48 X |

Primary Examiner—Arnold Rosenthal
Attorney, Agent, or Firm—Lyon & Lyon

[57] ABSTRACT

A slide valve is disclosed including a slider disposed between and slidable with respect to a pair of intercoupled valve body members. Selective positioning of the slider controls fluid flow through the slide valve. The slider includes at least one aperture and a tube communicating therewith. One of the valve body members includes at least one passageway with which the aperture of the slider can selectively communicate. A resilient pad with at least one aperture therethrough is positioned in a cavity in this valve body member and is disposed between the slider and the passageway. The other valve body member functions as a cap and is coupled with the first, and includes an elongated slot through which the tube of the slider extends. When the aperture of the slider overlaps or is aligned with the passageway of the first valve body member and the aperture of the pad, fluid communication exists through the valve. Conversely, the slider can be positioned to prevent fluid communication through the valve by moving the aperture of the slider adjacent another area of the pad. In alternative constructions, the first valve body member may include plural passageways, with the resilient pad having a like number of apertures, or the slider may have plural tubes which selectively communicate with the passageway of the first valve body member. Further modifications provide spring biasing of the slider member, as well as a screw adjustment to facilitate selecting the position of the aperture in the slider in controlling the rate of fluid flow. The various parts of the valve are formed of plastic material.

12 Claims, 8 Drawing Figures

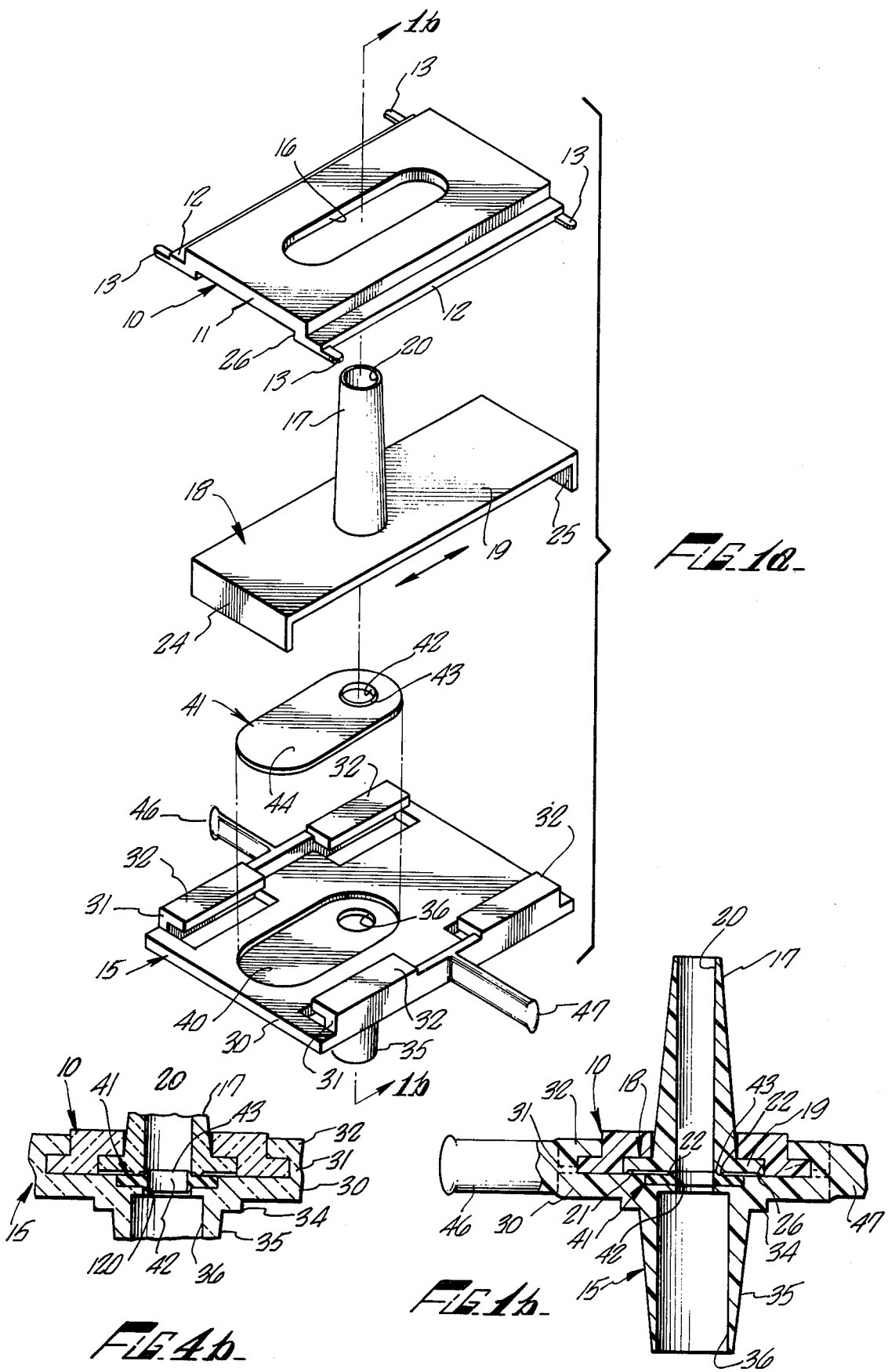

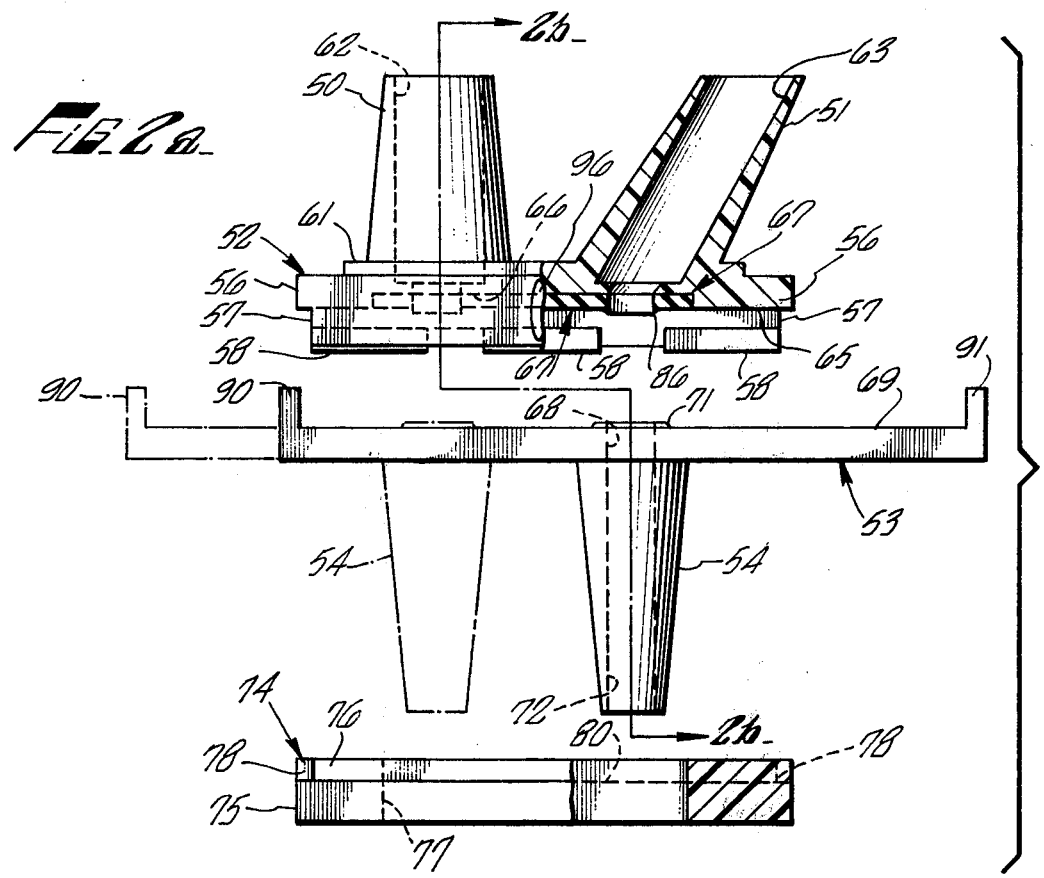
FIG. 2a.
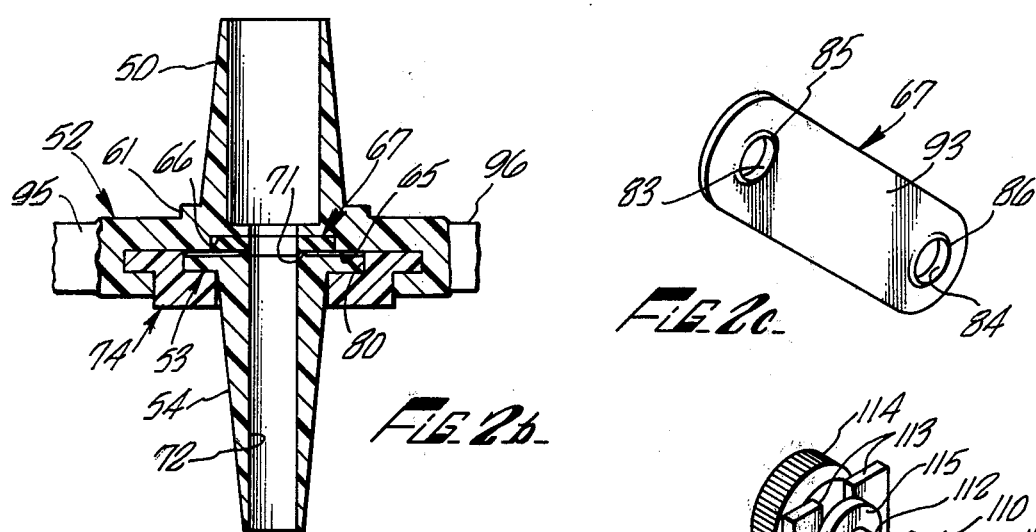
FIG. 2b.
FIG. 2c.
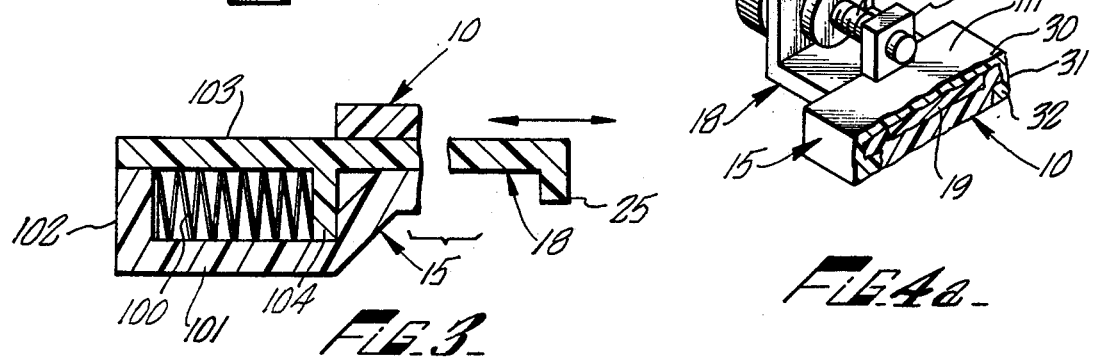
FIG. 3.
FIG. 4a.

SLIDE VALVE APPARATUS

CROSS-REFERENCE TO RELATED APPLICATION

This application is a continuation-in-part and division of application Ser. No. 377,801 filed July 9, 1973 now abandoned.

BACKGROUND OF THE INVENTION

This invention relates to slide valves which selectively provide fluid communication therethrough depending upon the position of an aperture in a slider. The slide valves of the present invention are particularly useful in medical applications, and in low to medium fluid pressure applications, where a simple and inexpensive, and disposable, plastic valve is desirable.

In the past, valves suitable for transferring fluid in medical applications, such as intravenous feeding of patients, required the use of pet-cock valves. These pet-cock valves typically are relatively bulky and cumbersome, especially when constructed to handle a relatively large amount of fluid flow. Further, with these prior valves, it was not readily apparent whether the valve was in an "on" or "off", or intermediate, position, thereby creating the possibility that the life of a patient could be in danger because of an erroneously assumed alignment.

SUMMARY OF THE INVENTION

A principal object of this invention is to provide an improved slide valve.

Another object of this invention is to provide a new form of disposable valve. A further object of this invention is to provide a slide valve which provides an improved seal between the inlet and outlet thereof, and one in which contamination of the movable slider thereof is minimized.

An additional object of this invention is to provide a new form of slide valve with a port which can selectively communicate with a pair of ports, and one which enables a minimum of disturbance of a patient when used in a medical application.

Another object of this invention is to provide a slide valve of relatively simple construction.

A further object of this invention is to provide a slide valve having an improved sealing member for the slider thereof.

Significant difficulties with prior art valves for such applications were the poor sealing characteristics, and the difficulty of manufacture because of the number of parts and intricacies of assembly.

Still further, when slide valves are used in a fluid transfer application, such as in the medical field, it is important that the fluid transfer and/or fluid control be accomplished with a minimum required movement of the valve control member, and that the valve be constructed to minimize contamination. It also is important in a medical application that fluid transfer valves be assembled without the use of glue, or the like, which may dislodge and be introduced into a patient's system or cause binding of moving parts of the valve.

The foregoing disadvantages and problems have been substantially eliminated by providing in a preferred embodiment a plastic slide valve, which can be manufactured and assembled inexpensively and, therefore, is disposable, including a slider positioned between interlocked or dovetailed valve body members for sliding movement with respect thereto. One body member includes a tube and a passageway therethrough. An elongated resilient pad is disposed in a cavity in this body member and has an aperture therethrough directly communicating with the passageway. The second valve body member is mechanically coupled with the first, and includes an elongated opening. The slider is disposed between the body members and has an aperture and a tube communicating therewith, and the tube extends through the elongated opening in the second valve body member which forms a cap. The slider, thus, has one surface that engages a surface of the pad. This surface of the slider preferably includes a raised ridge around the aperture thereof, and the mating surface of the pad preferably has a raised ridge around the aperture of the pad for sealing purposes which will be explained in greater detail subsequently. The valve body members and slider of the valve preferably are injection molded of plastic, and the pad is formed of a resilient material.

While the above preferred form of slide valve construction provides fluid communication between a single inlet and a single outlet and enables the user to readily see when the valve is "on" or "off", an alternative construction with similar features includes a pair of tubes and passageways in the first valve body member and a similar pair of apertures in the pad to form a double inlet (or outlet) port valve. In another alternative, the first valve body member and pad respectively have a single passageway and aperture, but the slider has a pair of tubes. These constructions allow, for example, the application of a second input fluid, such as an injection, through the valve in the same pathway that a fluid, such as an intravenous fluid, was administered to a patient. Thus, the application of a second fluid may be administered into the patient without removing or making a new insertion into the patient. The valve construction of the present invention makes it readily apparent which inlet is connected to the outlet passageway.

Additionally, a valve constructed according to the present invention may include a spring biased slider or a screw adjustable slider for facilitating liquid control.

BRIEF DESCRIPTION OF THE DRAWINGS

The present invention will be more completely understood from the following detailed description of embodiments of the invention, taken in conjunction with the drawings in which:

FIG. 1a is an exploded perspective view of an "on" and "off" slide valve constructed in accordance with this invention;

FIG. 1b is an assembled cross-sectional end view of the slide valve of FIG. 1a along the line 1b—1b;

FIG. 2a is an exploded side view of a double port slide valve constructed in accordance with this invention;

FIG. 2b is an assembled cross-sectional end view of the slide valve of FIG. 2a taken along line 2b—2b;

FIG. 2c is a perspective view of the resilient pad seal of the valve of FIGS. 2a–2b;

FIG. 3 is a partial side view, in cross-section, of a slide valve having a spring biased slider in accordance with this invention;

FIG. 4a is a partial perspective view of a screw adjustable slide valve in accordance with this invention; and FIG. 4b shows a further valve modification.

DESCRIPTION OF PREFERRED EMBODIMENTS

Turning now to the drawings, and first to FIGS. 1a–1b, a slide valve according to the present invention is shown and comprises a first, or upper, valve body member 10 having a flat upper section 11 and integrally formed male dovetail sections 12 extending outwardly from section 11. The four corners of the section 12 include integrally formed outwardly extending fingers 13 which lock the member 10 with a second, or lower, valve body member 15 as will be described later. The upper section 11 which forms a cap has an elongated slot 16 therein, and a hollow tube 17 of a slider 18 extends through this slot 16.

The slider 18 includes a flat elongated section 19 with an aperture communicating with the passageway 20 of the tube 17. The lower surface 21 (FIG. 1b) of the flat section 19 of the slider 18 includes a circular ridge 22 around the lower end of the passageway 20 for sealing purposes which will be described more completely subsequently. The slider 18 also includes integrally formed fingers or stops 24 and 25 at the ends thereof, and these facilitate sliding movement of the slider 18 in the direction of the arrows with respect to the valve body members 10 and 15 by hand, and can also serve as stops. For example, when the left stop 24 engages the left end of the valve body members 10 and 15, fluid communication is established through the valve; whereas, when the right stop 25 engages the right end of the valve body members 10 and 15, fluid communication therethrough is prevented. The inner surfaces of the dovetail sections 12 define a rectangular slot 26 within which the section 19 of the slider 18 is movably contained, and the tube 17 of the slider 18 can move freely back and forth in the elongated slot 16 of the first valve member 10.

The hollow tube 17 preferably is integrally formed with the section 19, and has an outer surface which is tapered in a conventional conical configuration so as to mate with typical medical devices and fittings (e.g., a luer taper). A luer lock (not shown) may be provided on the tube 17, and on any of the other ports of the valve embodiments herein, if desired, either by molding or adding the appropriate plastic part or parts, as by sonic cementing.

The second valve body member 15 includes a flat lower section 30, side sections 31 extending therefrom, and lips extending inwardly from sections 31 forming female dovetail sections 32. Each of the female dovetail sections 32 may comprise two lip portions as shown extending inwardly from each of the pair of side sections 31, or the dovetail section 32 extending inwardly from a side section 31 may be continuous rather than in two portions. A shoulder 34 (FIG. 1b) extends downwardly from the bottom surface of the lower section 30, and a hollow tube 35 extends downwardly from the shoulder. The afore-described portions of the valve body member 15 preferably are integrally formed of plastic, as by injection molding. The first valve body member 10 and the slider 18 preferably are similarly formed. The hollow tube 35 includes a passageway 36 therethrough, and through the lower section 30, to enable fluid communication with the passageway 20 of the slider 18. The outer surface of the tube 35 preferably is tapered and has a configuration similar to the outer surface of the tube 17 of the slider 18.

The lower valve body member 15 also includes an elongated cavity 40 in the upper surface of the lower section 30 thereof for receiving a resilient pad 41 which serves as a seal. The pad 41 includes an aperture 42 therethrough axially aligned with the passageway 36 in the tube 35 of valve body member 15. The pad 41 also preferably includes an integrally formed circular ridge or lip 43, and includes an elongated flat section 44. An exemplary material for the pad 41 is an elastomer such as Kraton sold by Shell. Soft rubber is suitable, but an artificial rubber such as Kraton is easier to mold, and Kraton 2705 is FDA approved for medical applications. Suitable materials for the valve body members 10 and 15 and the slider 18 are nylon, or a similar, relatively rigid, material.

The valve body member 15 may include fingers 46 and 47 which preferably are integrally formed and extend outwardly from the side of the sections 30–32 on each side of the lower valve body member 15. These fingers 46–47 enable the valve to be held by one hand while operating the slider 18 from one position to another. Since the tube 17 is part of the slider 18 and, therefore, moves with the slider, the state of the valve (either "on" or "off," or an intermediate position) is readily apparent because the position of the tube 17 with respect to the tube 35 is immediately apparent when looking at the valve.

In assembling the valve, the resilient pad 41 is inserted into the cavity 40. The tube 17 of the slider 18 is placed through the elongated slot 16 in the valve body member 10 with the section 19 of the slider 18 in the slot 26; that is, with the upper surface of the elongated flat section 19 of the slider against the lower surface of flat section 11 and the side edges of section 19 directly adjacent the inner surfaces of the section 12 of the body member 10. This assembly is then joined with the member 15 by sliding the male dovetail sections 12 of the body member 10 in between the female dovetail sections 32 of the valve body member 15. This operation, depending upon the length of the slider 18, may require that one of the stops 24 or 25 of the slider be raised thereby slightly bending the flat section 19 of the slider so as to enable engagement of the dovetail sections of members 10 and 15. In the assembly operation, the pair of fingers 13 extending from one end of the male dovetail section 12 are depressed to allow initial mating of the dovetail sections, and when the body member 10 is aligned with the body member 15, these fingers 13 extend past the ends (or "snap" out) of the side sections 31 of the body member 15. These fingers 13 thereby lock together the body members 10 and 15 longitudinally without requiring any adhesive, pins, or other joining members, and with the slider 18 properly disposed therebetween in the slot 26 for sliding movement. The dovetails lock together the body members 10 and 15 laterally. Although the provision of the fingers 13 is preferable, pins for locking the members 10 and 15 together can be used.

The circular ridge 22 extending downwardly from the lower surface 21 of the elongated flat section 19 of the slider 18 and around the aperture or passageway 20 therein serves to form an excellent seal with the resilient pad 41, particularly where the ridge 43 also is provided around the aperture 42 of the pad 41. In addition, the ridge 22 and the ridge 43 provide a seal between the lower surface 21 of the slider 18 and the upper surface of the resilient pad 41 when the valve is in the "off" position (slider moved to the left as seen in FIG. 1a). A good seal in the "off" position, as well as other positions, is particularly important in minimizing contamination of the valve which could be occasioned by air or foreign materials entering the aperture 20 of the slider 18 when the valve is in the "off" position, as well as the "on" or an intermediate position. It, thus, will be apparent that the resilient pad 41 serves to provide a seal from inlet to outlet of the valve when the valve is in the "on" position, as well as serves to provide a seal when the valve is in the "off" position, which seal is improved by the provision of the ridge 43 on the pad 41 and the ridge 22 on the slider 18. Although an O-ring seal can be used in place of the pad 41 and mounted axially with respect to the passageway 36 of the lower tube 35 to engage the lower surface of the slider 18, and the same will provide a reasonable seal in the "on" position of the valve, such an arrangement does not seal the aperture 20 of the slider 18 when in the "off" or intermediate position and air or other contaminants can make their way between the parts of the valve into the aperture 20 in this latter position. The valves of the present invention may be used with liquid or gases, although typical uses are for liquids in medical applications.

As will be apparent from FIG. 1a, when the stop member 24 of the slider 18 abuts the left face or edge of the assembled valve body, aperture 20 in the slider 18 is axially aligned with the passageway 20 of the upper tube 17, the aperture 42 in the pad 41 and the passageway 36 of the lower tube 35, thereby allowing complete fluid communication through the valve. Either the tube 17 or the tube 35 may serve as the inlet, with the other serving as the outlet, but in typical applications tube 17 is used as the inlet. Exemplary dimensions for the valve of FIG. 1a are approximately 2-3 centimeters (from the left to the right of the members 10 and 15 as viewed in FIG. 1a) and approximately 1.7 centimeters wide (members 10 and 15 as viewed from left to right in FIG. 1b, but not including the fingers 46 and 47 which typically are each about 0.7 cm long). The circular ridge 22 on the bottom surface of the slider 18 has a height of approximately 5 to 6 thousandths of an inch (approximately 0.127 to 0.152 millimeters), as does the circular ridge 43 on the resilient pad 41. The valve body members 10 and 15 and the slider 18 each may be integrally formed, as by injection molding, and preferably are made from a suitable type of plastic such as nylon as noted earlier, or a rigid polyethylene or polypropylene. In the event the valve is to be sterilized in an autoclave, a more heat resistant material, such as a polycarbonate, may be used since it will allow the slide valve to withstand higher heat. Valves of the present invention are suitable for low to medium pressure applications.

Turning now to FIGS. 2a-2c, the same illustrate another embodiment of a slide valve of the present invention substantially identical to that shown in FIGS. 1a-1b. However, in this construction, a valve body member 52 includes a pair of tubes 50 and 51 rather than the single tube 35 as shown in FIG. 1. The valve body member 52 has a flat upper section 56, side sections 57 extending therefrom, and lips extending inwardly from respective side sections 57 forming female dovetail sections 58, all substantially the same as sections 30-32 of valve body member 15 of FIG. 1. Each of the female dovetail sections 58 may comprise several lip portions 59 (three shown) extending inwardly from each of the pair of side sections 57, or each of the dovetail sections 58 extending inwardly from a side section 57 may be continuous rather than in three portions.

The valve of FIG. 2 includes a slider 53 having an integrally formed tube 54, and this valve enables selective communication between either of tubes 50-51 and the tube 54. This type of valve may be referred to as a two-port valve, and usually the tubes 50-51 serve as inlets; whereas, the tube 54 serves as an outlet. A typical application is for intravenous feeding wherein fluid normally communicates between tubes 50 and 54, but the slider 53 can be moved (to the right as shown in FIG. 2a) to allow communication between tubes 51 and 54 for enabling, for example, a doctor to administer an injection without disturbing or further injecting the patient.

Considering the construction of the valve of FIGS. 2a-2c further, a shoulder 61 extends upwardly from the upper part of section 56 of the valve body member 52, and the tubes 50 and 51 extend upwardly from this shoulder. The tubes 50-51 include respective passageways 62-63. A lower surface 65 of the top section 56 includes a cavity 66 therein for receiving a resilient pad 67 similar to the pad 41 of FIG. 1 and which is shown in greater detail in FIG. 2c. The slider 53 has an aperture 68 therein, and the upper surface 69 thereof has a circular ridge 71 like the ridge 22 of the slider 18 of the FIG. 1 valve construction. The aperture 68 in the slider 53 communicates with a passageway 72 in the tube 54 of the slider.

The valve of FIG. 2 also includes a valve body member 74, similar to valve body member 10 of the FIG. 1 valve, which includes a flat lower section 75 and integrally formed male dovetail sections 76 extending outwardly from the section 75. The valve body member 74 also includes an elongated slot 77 through which the tube 54 of the slider 53 extends and can slide back and forth. As with the valve of FIG. 1, the valve body member 74 preferably includes integrally formed outwardly extending fingers 78 at the four corners of the sections 76 which lock the body member 74 with the body member 52 like in the valve of FIG. 1. The top surface of section 75 and inner facing edges of sections 76 define a rectangular slot 80 in which the flat middle section of the slider 53 rides.

The resilient pad 67 includes apertures 83 and 84 axially aligned with the lower ends of the respective passageways 62 and 63 of the respective tubes 50 and 51 of the valve body section 52. This pad 67 fits within the cavity 66 in the upper section 56 of the valve body member 52, and also preferably includes circular ridges 85 and 86 on the lower surface thereof around the respective apertures 83 and 84. A flat area 93 is provided on the lower surface of the pad 67 intermediate the apertures 83 and 84 in the event it is desired that this two-port valve embodiment have an "off" position in between the two tubes 50 and 51. It should be noted that the ridge 71 normally will press into the mating surface of the pad 67 (as will the ridge 22 into pad 41 of the FIG. 1 valve), but the mating surface 69 and surface of pad 67 (and like surfaces in FIG. 1) are shown slightly exposed in the drawings for clarity of illustration of these components.

If an "off" position is desired, the side of the flat area 93 need only be sufficiently large to cover the aperture 68 and circular ridge 71 of the slider 53. Assuming the diameter of apertures 83-84 is approximately two millimeters, and the diameter of the circular ridge 71 to be approximately four millimeters, then the flat area 93 should be at least five to six millimeters and, of course, can be longer.

It is desirable that one of the two tubes 50–51 be inclined at an angle with respect to the other (such as the tube 51 being inclined at approximately 45° as shown) to enable the lower ends of the passageways 62–63 to be as close together as possible to both minimize the distance that the slider 53 must be moved in switching from one tube 50–51 to the other and to minimize possible contamination. By having the lower ends of the passageways 62–63 close together, the surfaces of the slider 53 do not extend outside the confines of the valve body members 52 and 74 in either position of the slider 53. This arrangement eliminates air or finger contamination of any surface portions of the slider 53 which comes in contact with either the pad 64 or the fluids being transferred by the valve. If an "off" position is not needed for the valve of FIG. 2, the lower ends of the passageways 62 may be disposed even closer together, and close enough to allow partial flow from both of the tubes 50–51 simultaneously to the outlet tube 54, as well as individual flow between 50 and 54 and 51 and 54, if desired.

The slider 53 preferably has fingers or stops 90–91 on the ends thereof, and the member 52 preferably has fingers 95–96 on the side like fingers 46–47 of the FIG. 1 single port valve. The pad 67 (and the pad 41 of the FIG. 1 valve) may alternatively be disposed in a cavity of the slider 53 if desired. In this case, circular ridges (like 71) are provided around the lower ends of passageways 62–63 to provide a good seal with the pad.

A two-port valve as shown in FIG. 2 may have a length of approximately three centimeters (from the left to the right of the members 52 and 74 as viewed in FIG. 2a), and a width of approximately 1.7 centimeters (from left to right as seen in FIG. 2b). The overall height from the upper end of the tube 50 to the lower end of the tube 54 may be approximately 2.5 centimeters in both the FIG. 1 and 2 valves. Thus, an exemplary valve of this construction is relatively small and compact, and a valve of the nature shown in FIG. 2 has been tested up to 40 psi (approximately 2.81 kg/cm$^2$) without noticeable deformation and without leakage.

As an alternative, individual cavities in the lower surface 65 of the upper section 56 of the valve body member 52 can be provided at the lower ends of the passageways 62–63, rather than the elongated cavity 66, with O-rings therein, for providing a seal with respect to the upper surface 69 of the slider 53; however, the elongated resilient pad 67 is preferred because is substantially minimizes or eliminates the possibility of leakage as well as the possibility of contaminants entering aperture 68 of the slider 53 from the exterior of the valve in between the slider 53 and valve body member 52.

As another alternative, which can simplify manufacture of a two-port valve of the nature shown in FIG. 2, the slider 53 may include two tubes 54 (in the same manner as these tubes are shown in solid lines and in phantom lines in FIG. 2a), and with the upper valve body member 52 including only a single tube 50. In this case, the upper valve body member 52 is substantially identical to the valve body member 15 of FIG. 1a with a single tube 35, the resilient pad is like pad 41 of FIG. 1a, the slider has two tubes as noted, and the second valve body member or cap (either 74 of FIG. 2a or 10 of FIG. 1a) has a longer elongated opening (77 or 16) so as to allow the two tubes of the slider to be selectively aligned with the single tube of the first valve body member. With this construction, the tubes of the slider typically will serve as inlets, and the single tube of the valve body member (e.g., 52 of FIG. 2a or 15 of FIG. 1a) will serve as the outlet. One of the tubes of the slider, in a typical application, will be used for intravenous feeding, but the slider can be moved to allow the second tube of the slider to enable an injection to be administered in a manner like that previously explained with respect to the two-port valve embodiment of FIG. 2. By including the two tubes on the slider rather than on one of the valve body members, tooling for molding of the valve parts is simplified. One of the two tubes can be inclined (like 51 of FIG. 2a) if desired. The pad has a single aperture if mounted on the valve body member (e.g., 15 or 52), but has two apertures if mounted in a cavity on the slider.

Although the tubes of the valve parts as shown and described herein have an exterior conical configuration and a cylindrically configured passageway, it is to be understood that reference to a tube encompasses other suitable configurations.

FIGS. 3 and 4 illustrate alternative additions to the constructions of the valves of FIGS. 1 and 2, and will be described as if the valve of FIG. 1 were so modified, although these modifications are applicable to both the valves of FIGS. 1 and 2. The modification shown in FIG. 3 involves a spring biasing arrangement whereby the slider 18 of the valve is maintained in a given state (either "on" or "off") by a spring 100. The lower valve body member 15 includes an integral extension 101 terminating in a finger 102. The lefthand side of the slider 18 has an integral extension 103 rather than the stop 24 shown in FIG. 1a, as well as a downwardly depending finger 104. The spring 100 is disposed in the cavity thus defined by the facing surfaces of fingers 102 and 104 (and side surfaces of 101, not shown) to thereby normally bias the slider 18 to the right as shown in FIG. 3 in which case the valve would normally be "on" if the modification of FIG. 3 were applied to the valve of FIG. 1a as these Figures are oriented in the drawings. The lower valve body member 15 preferably is molded to include the sections 101 and 102 as integral portions thereof.

Turning now to the modification of FIG. 4, the same involves a screw adjustment of the slider 18 to allow, for example, a doctor to accurately gauge the number of drops per minute for precise metering of fluid. It should be noted that the portion of the valve shown in FIG. 4 is oriented upside down with respect to the valve as shown in FIG. 1 so as to better illustrate the adjustment arrangement. In this modification, a finger 110 extends from the bottom surface 111 of the flat section 30 of the valve body member 15, and this finger is internally threaded to receive the end of a threaded member 112. The extreme end of the slider 18 has a bifurcated end or fork 113 through which the threaded member 112 extends. The outer extremity of the threaded member 112 has a head 114 fixed thereto, and a washer 115 is fixed to the threaded member so that rotation of the head 114 moves the slider 18 with respect to the valve body member 15. With this arrangement, the slider 18 can be precisely positioned to regulate the flow of fluid through the valve.

An additional modification of the valve of FIG. 1 is shown in FIG. 4b and is particularly useful with the screw adjustment modification of FIG. 4a. In the arrangement of FIG. 4b, the size, or diameter, of the aperture 42 in the resilient pad 41 preferably is slightly smaller than the size, or diameter, of the passageway 36 through the lower tube 35 of the valve body 15. In addition, the resilient pad 41 preferably includes a second circular ridge 120, like the upper ridge 43, on the bottom surface thereof. Also, at least the tube 35 (and the entire valve body member 15 if desired) is formed of clear plastic. With the tube 35 formed of clear plastic, the drops falling through the passageway 36 can be observed for facilitating accurate metering thereof, as in administering medicine. With the aperture 42 of the pad 41 being slightly smaller than the passageway 36, and preferably with the ridge 120, drops of liquid are temporarily held at the aperture 42 by surface tension so that such drops fall straight down the passageway 36 rather than running down the side of the passageway 36. This combination enhances accurate metering as well as facilitates accurate observation of the drops as they fall through the passageway 36. Although particularly applicable to the screw adjustment embodiment of FIG. 4a, the modification of 4b is equally applicable to the other valve arrangements shown and described.

While embodiments and applications of the present invention have been shown and described, it will be apparent to those skilled in the art that other modifications are possible without departing from the inventive concepts described herein.

What is claimed is:

1. A slide valve comprising first valve body means having an elongated opening therein and having integrally formed dovetail sections, said first body means being formed of plastic, second valve body means having a body section with a passageway therethrough, said passageway being substantially aligned with said elongated opening of said first body means, and said second body means having dovetail sections integrally formed with said body section and formed to cooperatively engage with the dovetail sections of said first body means, said body section of said second body means having an elongated cavity therein adjacent said passageway approximately coextensive with said elongated opening, and said second body means formed of plastic, slider means including a tube extending therefrom, said slider means being disposed between and separate from said first and second body means with said tube extending through said elongated opening of said first body means and being slidably movable with respect to said first and second body means to enable alignment of said tube and said passageway of said second body means when said slider means is positioned at a predetermined location to thereby enable fluid flow through said valve, said surface of said slider means opposite said tube including a circular rib extending therefrom substantially axially aligned with respect to the tube of said slider means, and an elongated resilient sealing means positioned in and coextensive with said cavity of second body means and having an aperture therethrough sealingly engaging the confronting surface of said slider means, said sealing means aligned with the passageway in said second valve body means, said sealing means having a sealing surface maintained in sealing contract with the confronting surface of said slider means opposite said tube thereof to provide a seal around said aperture for the tube of said slider means when in position for fluid flow and a seal closing said aperture when the tube of said slider means is displaced from said aperture, whereby, irrespective of the position of said slider means, with respect to said sealing means, leakage of fluid from the passageway of said second valve body means, or the tube of said slider means or entrance of extraneous fluid into said passageway or tube, is prevented.

2. A slide valve for passage of contaminable fluids comprising first plastic valve body means having an elongated opening therein, second plastic valve body means having a body section with a passageway therethrough, said passageway being substantially aligned with said elongated opening of said first body means, and said body section of said second body means having an elongated shallow cavity therein adjacent said passageway, said first and second body means being coupled together and forming a guide passage therebetween, a resilient sealing plate sealingly received in said cavity, and having an aperture therethrough in registry with the passageway in said body means, and slider means including a tube extending therefrom with an opening therethrough, said slider means being disposed in said guide passage with said tube extending through said elongated opening of said first body means and being slidably movable with respect to said first and second body means to selectively enable alignment of said tube with the aperture in said sealing plate and the passageway of the second body means when said slider means is positioned at a predetermined location to thereby enable fluid flow through said valve, said surface of said slider means opposite said tube including a circular rib extending therefrom substantially axially aligned with respect to the opening of the tube of said slider means, and said surface of said sealing plate including a raised circular ridge disposed substantially coaxially with respect to the aperture therethrough, said sealing plate having a surface in contact with a surface of said slider means opposite said tube thereof to provide a seal for sealing the opening of the tube of said slider means when said slider means is positioned out of alignment with the passageway in said second plastic valve body, and to provide a seal surrounding the tube when its aperture is in alignment with the passageway in said second plastic valve, the resilient sealing plate also being entirely enclosed to prevent contamination by contact or by entrance of extraneous fluid irrespective of the position of the slider means.

3. A slide valve for control of contaminable fluids, comprising a body means defining a flat guideway open at its extremities, and having confronting wall surfaces, one of the wall surfaces having an elongated slot, the opposed wall surface having a shallow depression at least coextensive with the slot, a resilient sealing plate received in the depression and forming a sealing surface essentially coplanar with the wall surface surrounding the depression, a slider slidably received in the guide passage disposed in sealing engagement with the sealing plate, the sealing plate having at least one perforation therethrough, the body means having at least one tube defining a flow passage in registry with the perforation, the slider having at least one tube extending through the elongated slot in the body means and defining a flow passage having an end in sealing engagement with the sealing plate and movable between a position in registry with the perforation therein for flow of fluid through the slide valve, and a position closed by the sealing plate, and the sealing plate being in sealing engagement with and covered by the surface of the depression, and being completely covered by the slider in all positions thereof, thereby to isolate the entire sealing plate from extraneous contamination; and the margins of the perforation being sealed with respect to the body means and the slider in both open and closed positions to prevent leakage into or out of the tube passages.

4. A slide valve for control of contaminable fluids, comprising a body means defining a flat guideway open at its extremities, and having confronting wall surfaces, one of the wall surfaces having an elongated slot, the opposed wall surface having a shallow depression at least coextensive with the slot, a resilient sealing plate received in the depression and forming a sealing surface essentially coplanar with the wall surface surrounding the depression, a slider slidably received in the guide passage disposed in sealing engagement with the sealing plate, the sealing plate having at least one perforation therethrough, the body means having at least one tube defining a flow passage in registry with the perforation, the slider having at least one tube extending through the elongated slot in the body means and defining a flow passage having an end in sealing engagement with the sealing plate and movable between a position in registry with the perforation therein for flow of fluid through the slide valve, and a position closed by the sealing plate, the sealing plate being in sealing engagement with and covered by the surface of the depression, and being completely covered by the slider in all positions thereof, thereby to isolate the entire sealing plate from extraneous contamination; and the margins of the perforation being sealed with respect to the body means and the slider in both open and closed positions to prevent leakage into or out of the tube passages, and the slider protruding beyond the body means and provided with stops at opposite ends engageable with the body means to limit the movement of the slider.

5. A slide valve as in claim 4, wherein a spring yieldably maintains the slider at a preselected position with respect to the body means.

6. A slide valve as in claim 4, wherein a screw drive means moves the slider with respect to the body means.

7. A slide valve comprising first valve body means having an elongated opening therein and having integrally formed dovetail sections, said first body means being formed of plastic, second valve body means having a body section with a passageway therethrough, said passageway being substantially aligned with said elongated opening of said first body means, and said second body means having dovetail sections integrally formed with said body section and formed to cooperatively engage with the dovetail sections of said first body means, said body section of said second body means having an elongated cavity therein adjacent said passageway approximately coextensive with said elongated opening, and said second body means being formed of plastic, slider means including a tube extending therefrom, said slider means being disposed between and separate from said first and second body means with said tube extending through said elongated opening of said first body means and being slidably movable with respect to said first and second body means to enable alignment of said tube and said passageway of said second body means when said slider is positioned at a predetermined location to thereby enable fluid flow through said valve, and an elongated resilient sealing means positioned in and coextensive with said cavity of second body means and having an aperture therethrough and including a raised circular ridge disposed substantially coaxially with respect to the aperture therethrough.

8. A slide valve comprising first valve body means having an elongated opening therein and having integrally formed dovetail sections, said first body means being formed of plastic, second valve body means having a body section with a passageway therethrough, said passageway being substantially aligned with said elongated opening of said first body means, and said second body means having dovetail sections integrally formed with said body section and formed to cooperatively engage with the dovetail sections of said first body means, said body section of said second body means having an elongated cavity therein adjacent said passageway approximately coextensive with said elongated opening, and said second body means being formed of plastic, said body section of said second valve body means including a tube with said passageway extending therethrough, said tube being formed of transparent plastic, and said passageway therethrough being of larger size than the size of the aperture in said resilient sealing means and said sealing means having a circular lip around the aperture therethrough and extending into said passageway to enable fluid flow in the form of droplets through said passageway, slider means including a tube extending therefrom, said slider means being disposed between and separate from said first and second body means with said tube extending through said elongated opening of said first body means and being slidably movable with respect to said first and second body means to enable alignment of said tube and said passageway of said second body means when said slider means is positioned at a predetermined location to thereby enable fluid flow through said valve, and an elongated resilient sealing means positioned in and coextensive with said cavity of second body means and having an aperture therethrough sealingly engaging the confronting surface of said slider means, said sealing means aligned with the passageway in said second valve body means, said sealing means having a sealing surface maintained in sealing contact with the confronting surface of said slider means opposite said tube thereof to provide a seal around said aperture for the tube of said slider means when in position for fluid flow and a seal closing said aperture when the tube of said slider means is displaced from said aperture, whereby, irrespective of the position of said slider means, with respect to said sealing means, leakage of fluid from the passageway of said second valve body means, or the tube of said slider means or entrance of extraneous fluid into said passageway or tube, is prevented.

9. A slide valve for control of contaminable fluids, comprising a body means defining a flat guideway open at its extremities, and having confronting wall surfaces, one of the wall surfaces having an elongated slot, the opposed wall surface having a shallow depression at least coextensive with the slot, a resilient sealing plate received in the depression and forming a sealing surface essentially coplanar with the wall surface surrounding the depression, a slider slidably received in the guide passage disposed in sealing engagement with the sealing plate, the sealing plate having at least one perforation therethrough, the body means having at least one tube defining a flow passage in registry with the perforation, the slider having at least one tube extending through the elongated slot in the body means and defining a flow passage having an end in sealing engagement with the sealing plate and movable between a position in registry with the perforation therein for flow of fluid through the slide valve, and a position closed by the sealing plate, the sealing plate being in sealing engagement with and covered by the surface of the depression, and being completely covered by the slider in all positions thereof, thereby to isolate the entire sealing plate from extraneous contamination; and the margins of the perforation being sealed with respect to the body means and the slider in both open and closed positions to prevent leakage into or out of the tube passages, and the tube of the body means being transparent and larger than the perforation in the sealing plate and its end adjacent the perforation is constricted, whereby downward fluid flow into the tube from the constricted end is caused to form droplets to indicate, by the sequence rate of the droplets, the rate of flow.

10. A slide valve for control of contaminable fluids, comprising a body means defining a flat guideway open at its extremities, and having confronting wall surfaces, one of the wall surfaces having an elongated slot, the opposed wall surface having a shallow depression at least coextensive with the slot, a resilient sealing plate received in the depression and forming a sealing surface essentially coplanar with the wall surface surrounding the depression, a slider slidably received in the guide passage disposed in sealing engagement with the sealing plate, the sealing plate having at least one perforation therethrough, the body means having at least one tube defining a flow passage in registry with the perforation, the slider having at least one tube extending through the elongated slot in the body means and defining a flow passage having an end in sealing engagement with the sealing plate and movable between a position in registry with the perforation therein for flow of fluid through the slide valve, and a position closed by the sealing plate, the sealing plate being in sealing engagement with and covered by the surface of the depression, and being completely covered by the slider in all positions thereof, thereby to isolate the entire sealing plate from extraneous contamination; and the margins of the perforations being sealed with respect to the body means and the slider in both open and closed positioned to prevent leakage into or out of the tube passages, said body means being provided with two tubes defining flow passages, the sealing plate being provided with two perforations in registry therewith, and the slider being movable for communication with either flow passage.

11. A slide valve for control of contaminable fluids, comprising a body means defining a flat guideway open at its extremities, and having confronting wall surfaces, one of the wall surfaces having an elongated slot, the opposed wall surface having a shallow depression at least coextensive with the slot, a resilient sealing plate received in the depression and forming a sealing surface essentially coplanar with the wall surface surrounding the depression, a slider slidably received in the guide passage disposed in sealing engagement with the sealing plate, the sealing plate having at least one perforation therethrough, the body means having at least one tube defining a flow passage in registry with the perforation, the slider having at least one tube extending through the elongated slot in the body means and defining a flow passage having an end in sealing engagement with the sealing plate and movable between a position in registry with the perforation therein for flow of fluid through the slide valve, and a position closed by the sealing plate, the sealing plate being in sealing engagement with and covered by the surface of the depression, and being completely covered by the slider in all positions thereof, thereby to isolate the entire sealing plate from extraneous contamination; and the margins of the perforation being sealed with respect to the body means and the slider in both open and closed positions to prevent leakage into or out of the tube passages, and the slider being provided with two tubes defining flow passages, either passages being movable into registry with the perforation in the sealing plate.

12. A slide valve for control of contaminable fluids, comprising a body means defining a flat guideway open at its extremities, and having confronting wall surfaces, one of the wall surfaces having an elongated slot, the opposed wall surface having a shallow depression at least coextensive with the slot, a resilient sealing plate received in the depression and forming a sealing surface essentially coplanar with the wall surface surrounding the depression, a slider slidably received in the guide passage disposed in sealing engagement with the sealing plate, the sealing plate having at least one perforation therethrough, the body means having at least one tube defining a flow passage in registry with the perforation, the slider having at least one tube extending through the elongated slot in the body means and defining a flow passage having an end in sealing engagement with the sealing plate and movable between a position in registry with the perforation therein for flow of fluid through the slide valve, and a position closed by the sealing plate, the sealing plate being in sealing engagement with and covered by the surface of the depression, and being completely covered by the slider in all positions thereof, thereby to isolate the entire sealing plate from extraneous contamination; and the margins of the perforation being sealed with respect to the body means and the slider in both open and closed positions to prevent leakage into or out of the tube passages;

the body means including two components, having mutually engageable initially slidable elements forming lateral margins of the guideway.

* * * * *